United States Patent
Tran et al.

(10) Patent No.: US 6,909,095 B2
(45) Date of Patent: Jun. 21, 2005

(54) SYSTEM AND METHOD FOR TERAHERTZ IMAGING USING A SINGLE TERAHERTZ DETECTOR

(75) Inventors: Phuc G. Tran, Richmond, VA (US); Kenneth H. Shafer, Sutherland, VA (US)

(73) Assignee: Philip Morris USA Inc., Richmond, VA (US)

( * ) Notice: Subject to any disclaimer, the term of this patent is extended or adjusted under 35 U.S.C. 154(b) by 92 days.

(21) Appl. No.: 10/454,152

(22) Filed: Jun. 4, 2003

(65) Prior Publication Data

US 2004/0155193 A1 Aug. 12, 2004

Related U.S. Application Data

(63) Continuation-in-part of application No. 10/365,029, filed on Feb. 12, 2003.

(51) Int. Cl.[7] .................................................. G01J 5/08
(52) U.S. Cl. ..................... 250/341.1; 250/340; 250/330
(58) Field of Search .............................. 250/341.1, 340, 250/330

(56) References Cited

U.S. PATENT DOCUMENTS

| | | | |
|---|---|---|---|
| 5,050,989 A | | 9/1991 | Van Tassel et al. |
| 5,530,778 A | * | 6/1996 | Rast ............... 385/24 |
| 5,623,145 A | | 4/1997 | Nuss |
| 5,710,430 A | | 1/1998 | Nuss |
| 5,729,017 A | | 3/1998 | Brener et al. |
| 5,762,075 A | | 6/1998 | Hoppe et al. |
| 5,789,750 A | | 8/1998 | Nuss |
| 5,862,287 A | | 1/1999 | Stock et al. |
| 5,894,125 A | | 4/1999 | Brener et al. |
| 5,923,036 A | | 7/1999 | Tague, Jr. et al. |
| 5,939,721 A | | 8/1999 | Jacobsen et al. |
| 6,078,047 A | | 6/2000 | Mittleman et al. |
| 6,519,076 B2 | * | 2/2003 | Fisher et al. ............... 359/326 |
| 6,525,862 B2 | * | 2/2003 | Fisher et al. ............... 359/278 |
| 6,665,075 B2 | * | 12/2003 | Mittleman et al. ......... 356/450 |
| 2002/0020806 A1 | | 2/2002 | Almi |
| 2004/0155192 A1 | * | 8/2004 | Tran et al. ............... 250/341.1 |

FOREIGN PATENT DOCUMENTS

| | | |
|---|---|---|
| GB | 2 347 835 A | 9/2000 |
| GB | 2 350 673 A | 12/2000 |
| GB | 2 360 186 A | 9/2001 |
| WO | WO 99/49297 | 9/1999 |

OTHER PUBLICATIONS

Martin C. Nuss, "Chemistry is Right for T-Ray Imaging," *IEEE*, pp. 25–30 (Mar. 1996).

* cited by examiner

*Primary Examiner*—David Porta
*Assistant Examiner*—Christine Sung
(74) *Attorney, Agent, or Firm*—Connolly Bove Lodge & Hutz LLP (57) ABSTRACT

A system and method for THz imaging utilizing a single THz detector that detects an image of a large area and provides good spatial details (high resolution). In one aspect, the system can individually modulate a different pixel of an image. The system could be a series of masks. Each mask may include holes that may be turned on/off with a distinct pattern from all of the other holes. Once the data for each mask has been received, the data for each hole may be extracted according to its modulation pattern. Another modulation system may include a micro-mirror array that deflects the THz signal towards or away from the THz detector.

15 Claims, 6 Drawing Sheets

SYSTEM AND METHOD FOR TERAHERTZ IMAGING USING A SINGLE TERAHERTZ DETECTOR

CROSS REFERENCE TO RELATED APPLICATIONS

The present application is a continuation-in-part of application Ser. No. 10/365,029, filed Feb. 12, 2003, the disclosure of which being incorporated by reference herein in its entirety.

BACKGROUND OF THE INVENTION

A. Field of the Invention

The present invention relates generally to imaging in the terahertz (THz) frequency range, and, more particularly to a system and method for terahertz imaging that utilizes a single terahertz detector.

B. Description of the Related Art

A terahertz ("THz") detector or receiver detects electromagnetic energy or radiation with frequencies in the terahertz range (fractions to tens of terahertz, where terahertz= $10^{12}$ Hertz). A typical THz system consists of a THz transmitter and a THz detector. The transmitter transmits a THz beam that passes through or reflects from an object under examination. The THz detector detects the THz energy that passes through or reflects from the object, and reaches its collecting area over time. Such a system may be considered a 1×1 array or a single pixel system. The significance of this description can be seen by, for example, a digital camera that is characterized by its number of pixels. Each pixel of the camera is just a single detector capable of detecting electromagnetic energy in the visible wavelength. To obtain an image of a large area having good spatial details (resolution), a large array of detectors is needed in the imaging system. This is why a digital camera with more pixels has better resolution (e.g., a clearer and sharper picture) and costs more.

The same principle applies to THz imaging. Conventional THz systems detect THz energy over a certain area defined by the size of a THz beam. With a single THz detector (one pixel), a tradeoff needs to be made between the size of the imaging area and the spatial resolution. This is because the energy from different parts of the imaging area arrives at the single THz detector about the same time, and cannot be separated to get spatial details. To obtain good spatial resolution with conventional THz systems, the THz beam must have a small beam size, which reduces the area that can be imaged. To image a larger area, the small THz beam may be scanned over the area to be imaged or the area is scanned across the THz beam. To date, the only known way to create a THz array imager is to utilize an array of THz detectors. Unfortunately, it is very difficult and expensive to fabricate an array of THz detectors for a THz imaging system.

Thus, there is a need in the art for a single terahertz detector imaging system that detects an image of a large area and provides good spatial details (high resolution) without the need to scan a THz beam across an entire sample or scan the entire sample across the THz beam.

SUMMARY OF THE INVENTION

The present invention solves the problems of the related art by providing a system and method for THz imaging that uses a single THz detector that detects an image of a large area and provides good spatial details (high resolution) without scanning the THz beam across the entire sample or vice versa.

In accordance with the purpose of the invention, as embodied and broadly described herein, the invention is broadly drawn to a system and method for THz imaging by: (1) converting spatial information in a THz beam into time-multiplexed information that can be computer processed to recover the spatial information (hereinafter referred to as "the time-multiplexing technique"); (2) modulating different spatial regions (i.e., pixels) with different frequencies (or patterns) that can be computer processed to recover the spatial information (hereinafter referred to as "the pixel-modulation technique"); and/or (3) a combination of the time-multiplexing and pixel-modulation techniques.

In one aspect of the invention, the time-multiplexing technique, the THz beam passes through an object to be imaged, and a THz fiber bundle having a plurality of THz fibers collect the THz beam on the other side of the object and transmit the beams to a single THz detector. Each THz fiber imparts a different time delay to the beam traveling therein. Therefore, the spatial information, as represented by the physical location of the fibers, is converted into time information in the form of time delays. The amount of time delay through a THz fiber can be controlled in two ways: (1) by changing the refractive index n of the THz fiber; or (2) by changing the length l of the THz fiber. Knowing the distance each part of the imaging area must travel (hence the time it takes) before reaching the THz detector, one can recover the spatial information from the time data.

In a variation of the time-multiplexing technique, the THz fiber bundle may be replaced with a mask having an array of pixels (or spatial regions). Each pixel may be a composite of two or more materials of different refractive indices, including holes. A hole is a material with a refractive index of one. The THz beams or pulses pass through the object to be imaged and then through the mask, and are transmitted to the THz detector. Each pixel of the mask imparts a different time delay on the THz beam traveling inside it. Therefore, the spatial information is converted to time information in the form of time delays. A variation of the invention is to have the array of THz fibers or the mask in front of the object.

In another aspect of the invention, the pixel-modulation technique, each pixel is turned on/off with a distinct pattern from all of the other pixels. Even though there is a single THz detector, the THz energy emanating from each pixel can be identified because of the distinct on/off pattern of each pixel. To turn each pixel on and off, one variation of the pixel-modulation technique uses a series of masks. Each mask may have a set of holes corresponding to a set of pixels being in their ON states. Different masks may have different sets of pixels being ON. The masks may be mounted in front of or behind the object, on a translation stage. Each mask is moved into position (in front of or behind the object) and measurements are taken. Knowing the on/off pattern of each pixel, the measured data may be computer processed to obtain the THz data for each pixel. The modulation patterns for the pixels may be Hadamard matrix, S matrix, or random. This technique provides an increased signal-to-noise ratio as compared to using a single hole (i.e., a single pixel) and moving the hole location from one measurement to the next. Variations of this arrangement include using a spatial light modulator to turn the pixels on and off electronically, and using a micro-mirror array to turn the pixels on and off electronically. These variations eliminate the need for different masks and a translating stage.

Once the data for each mask has been received, the data for each pixel is extracted according to its modulation pattern. This data is in the time domain and can be used in standard imaging (e.g., intensity or time delay imaging). The data may also be Fourier transformed for spectroscopic imaging.

Another aspect of the invention is to use a combination of the time-multiplexing technique and the pixel-modulation technique. The pixel-modulation technique (whether by mask, spatial light modulator, or micro-mirror array) may be used to provide fine spatial resolution while the time-multiplexing technique (whether by fibers or mask) may be used to provide coarse spatial resolution. Another variation is to interchange the functions of these two techniques.

In still another aspect of the invention, a THz transmitter (s) is not required, and the passive THz energy emitted directly from an object is measured with a single THz detector. The THz emission from an object may be focused onto, for example, a micro-mirror array that reflects the THz energy towards (an "on" state) or away from (an "off" state) the THz detector. The movable individual mirror(s) of micro-mirror array may be used to turn pixels on or off for Hadamard transform multiplexing.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description. It is to be understood that both the foregoing general description and the following detailed description are exemplary and explanatory only and are not restrictive of the invention, as claimed.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF EMBODIMENTS OF THE INVENTION

The following detailed description of the invention refers to the accompanying drawings. The same reference numbers in different drawings identify the same or similar elements. Also, the following detailed description does not limit the invention. Instead, the scope of the invention is defined by the appended claims and equivalents thereof.

Figure 1:
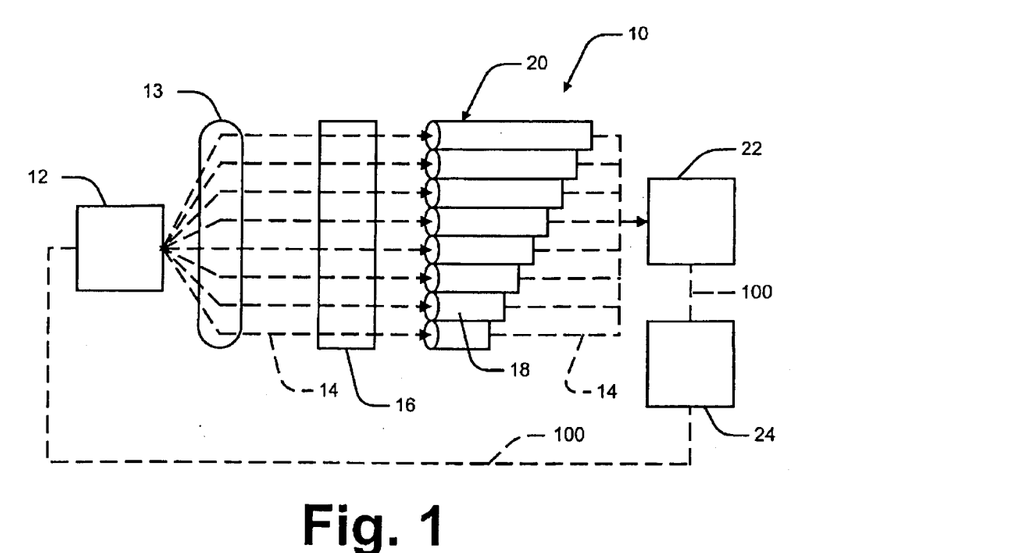
FIG. 1 is a schematic elevational view showing a system for THz imaging and utilizing a single THz detector and a THz fiber bundle in accordance with an embodiment of the present invention.

Referring now specifically to the drawings, a THz imaging system according to an embodiment of the present invention is illustrated in FIG. 1 and shown generally as reference numeral 10. The THz imaging system 10 has particular application in imaging any type of object. As used herein, the term "object" or "sample" encompasses any object or sample to be THz imaged. There are many potential commercial applications in which THz imaging may be utilized. Promising applications include industrial quality and process control, package inspection, moisture analysis, contamination measurements, and chemical analysis. Thus, the object and the analysis to be performed on the object are left open to the user of the THz imaging system. The system of the present invention provides pixel-level data, and it is up to the user to analyze the data as needed for the application in interest.

As shown in FIG. 1, THz imaging system 10 comprises at least one THz transmitter 12, and possibly a multitude of THz transmitters 12, for transmitting THz pulses, beams, or rays 14 through a collimating lens 13 and an object 16, and a single THz detector or receiver 22 for receiving the THz pulses 14 transmitted through or reflected from object 16 and generating electrical signals corresponding to the received THz pulses 14. A conventional computer 24 receives the electrical signals outputted by THz detector 22 and THz transmitters 12, via communication link 100, and calculates a desired property of object 16. Computer 24 may be used to image any object 16 capable of being imaged using a THz imaging system. Thus, the present invention is not limited by the specific object 16 under observation.

THz imaging system 10 of the present invention provides an image of a large area and also provides an image having good spatial details (high resolution). Conventionally, one way to accomplish this result is to provide a large array of THz detectors in the imaging system. However, it is very difficult and expensive to fabricate an array of THz detectors for a THz imaging system. Another way to accomplish this result is to obtain an image by scanning the THz beam across the sample or by the scanning the sample across the THz beam. This is known as rastering. Rastering, unfortunately, is very slow because of the mechanical nature of the scanning apparatus. The present invention eliminates the need for rastering by using time multiplexing and a single THz detector 22. THz system 10 converts spatial information in THz pulse 14 into a time-multiplexed data stream (i.e., THz energy from different areas arrives at THz detector 22 at a sufficiently separated time for identification purposes) that can be processed by computer 24 to recover the spatial details.

In one embodiment of the present invention, as shown in FIG. 1, the time multiplexing of spatial information is achieved by forcing the THz energy from different areas of an image to travel different distances before reaching THz detector 22. Knowing the travel distance for each part of the imaged area (THz pulse 14), and hence the time each pulse 14 takes before reaching THz detector 22, computer 24 can recover the spatial information from the time data. FIG. 1 shows a linear array imager made up of THz fibers or light pipes 18 arranged in a THz fiber bundle 20 as one example of how to time multiplex spatial information. THz beams or pulses 14 pass through object 16, are collected by THz fibers 18, and are transmitted to THz detector 22. Each THz fiber 18 imparts a different time delay on the THz beam 14 traveling inside. Therefore, the spatial information is converted to time information in the form of time delays. The amount of time delay through each THz fiber 18 can be controlled in two ways. The time it takes for THz energy to travel through a THz fiber 18 of length l is $t=nl/c$, where n is the refractive index of the THz fiber 18 and c is the speed of light. Thus, the amount time delay can be controlled by changing the refractive index n of the THz fiber 18, or, alternatively, by changing the length l of the THz fiber 18. Since the length of each THz fiber 18 is known, it is known when the THz pulse 14 from each THz fiber 18 reaches THz detector 22. This information is used by computer 24 to separate the THz pulses 14. In practice, all of the THz fibers 18 may be blocked, except one, to precisely determine the window of arrival for each THz pulse 14. This is performed only once for calibration purposes.

Although only eight THz fibers 18 are shown in a linear array in FIG. 1, any number and arrangement of THz fibers 18 may be provided. The number and geometry of THz fibers 18 only depend upon the size and geometry of the imaging area required. Thus, if an N×M array resolution is needed, then an N×M array of THz fibers 18 should be used. A variation of the FIG. 1 embodiment of the present invention, is to place THz fibers 18 before object 16 instead of after it. Furthermore, although FIG. 1 shows THz fiber bundle 20 and THz detector 22 being arranged on the opposite side of object 16 as THz transmitters 12 (this is a transmission mode arrangement), THz fiber bundle 20 and THz detector 22 may also be provided on the same side of object 16 as THz transmitters 12 to capture reflected THz beams 14 (this is a reflective mode arrangement).

Collimating lenses 13 are preferably provided between object 16 and THz transmitter 12 to make THz pulses 14 parallel. High density polyethylene (HDPE), low density polyethylene (LDPE), or alumina lenses are preferred but other types of lenses may be used as long as they do not appreciably effect the THz radiation.

Each THz transmitter 12 may be any conventional THz transmitter. The radiation emanating from each THz transmitter 12 preferably will be from 0.1 terahertz (THz) to 100 terahertz (THz), but any electromagnetic frequency above this preferred range is possible, as long as it is still within the THz frequency range.

Similarly, THz detector 22 may be any conventional THz detector. THz detector 22 is configured to detect electromagnetic radiation in the THz range, as it passes through object 16. THz detector 22 may be placed at any position adjacent to object 16, so as to detect transmitted, reflected, refracted or scattered radiation. In a transmission mode measurement, the THz detector 22 measures the THz radiation that passes through object 16. In a reflection mode measurement, the THz detector 22 measures light that is reflected from object 16. The same information is provided via either mode, and thus, either mode may be used with the present invention. THz detector 22 then generates an electrical signal which is collected and analyzed by computer 24, via communication link 100.

Figure 6:
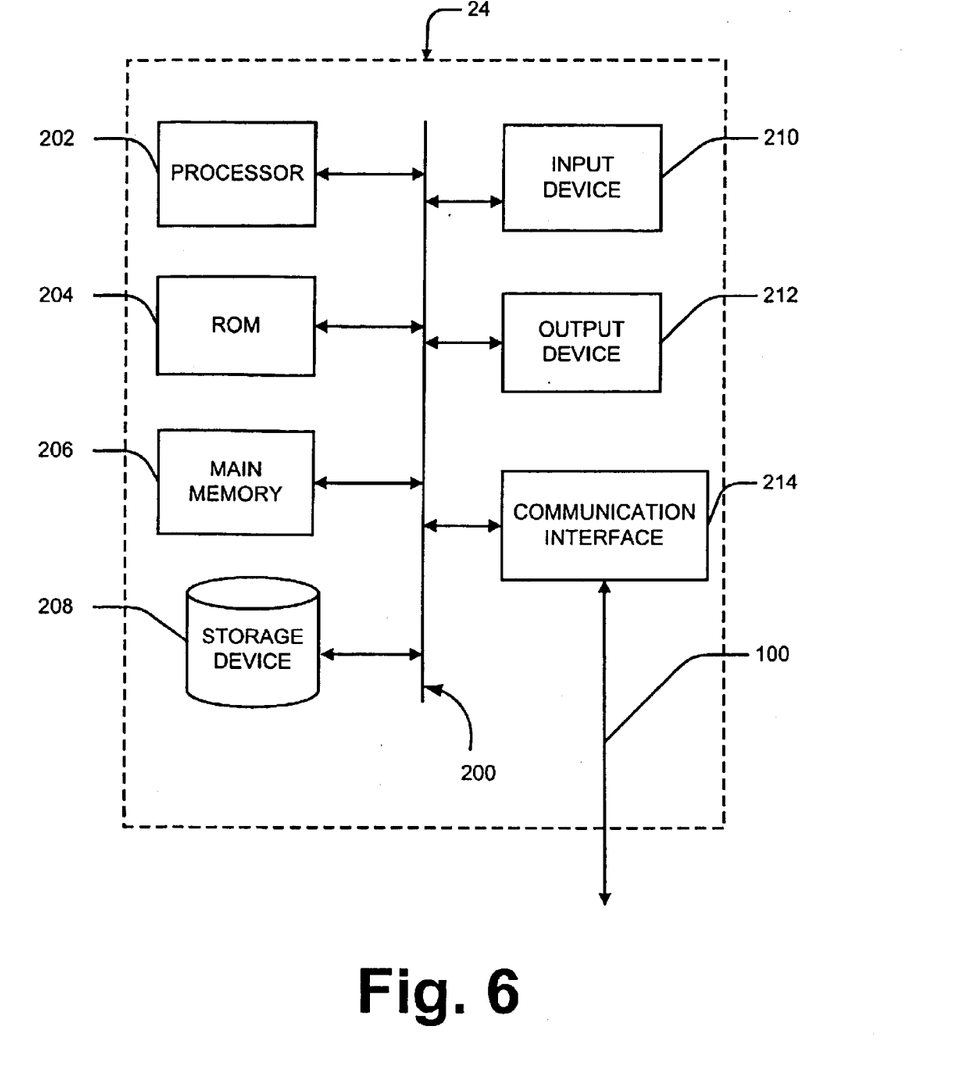
FIG. 6 is a schematic diagram showing a central processing unit of the systems shown in FIGS. 1–3.

Referring to FIG. 6, computer 24 may be any conventional computing device, and thus includes a bus 200 interconnecting a processor 202, a read-only memory (ROM) 204, a main memory 206, a storage device 208, an input device 210, an output device 212, and a communication interface 214. Bus 200 is a network topology or circuit arrangement in which all devices are attached to a line directly and all signals pass through each of the devices. Each device has a unique identity and can recognize those signals intended for it. Processor 202 includes the logic circuitry that responds to and processes the basic instructions that drive computer 24. ROM 204 includes a static memory that stores instructions and date used by processor 202.

Computer storage is the holding of data in an electromagnetic form for access by a computer processor. Main memory 206, which may be a RAM or another type of dynamic memory, makes up the primary storage of computer 24. Secondary storage of computer 24 may comprise storage device 208, such as hard disks, tapes, diskettes, Zip drives, RAID systems, holographic storage, optical storage, CD-ROMs, magnetic tapes, and other external devices and their corresponding drives. Main memory 206 and/or storage device 208 may store any of the THz data retrieved by any of the systems of the present invention.

Input device 210 may include a keyboard, mouse, pointing device, sound device (e.g. a microphone, etc.), biometric device, or any other device providing input to computer 24. Output device 212 may comprise a display, a printer, a sound device (e.g. a speaker, etc.), or other device providing output to computer 24. Communication interface 214 may include network connections, modems, or other devices used for communications with other computer systems or devices.

Communication links 100 may be wired, wireless, optical or a similar connection mechanisms. "Wireless" refers to a communications, monitoring, or control system in which electromagnetic or acoustic waves carry a signal through atmospheric space rather than along a wire. In most wireless systems, radio-frequency (RF) or infrared (IR) waves are used. Some monitoring devices, such as intrusion alarms, employ acoustic waves at frequencies above the range of human hearing.

Computer 24 consistent with the present invention may perform the task of identifying the THz data corresponding to each pixel of the image of object 16. Computer 24 performs this task in response to processor 202 executing sequences of instructions contained in a computer-readable medium, such as main memory 206. A computer-readable medium may include one or more memory devices and/or carrier waves. In the time-multiplexing technique, this involves identifying the time region where the THz pulses 14 of a pixel arrive at THz detector 22. Computer 24 then assigns any data that arrives within that time region to that pixel. In the pixel-modulation technique, computer 24 extracts the THz data of a given pixel by using the modulation pattern of the given pixel. Any THz data that has that particular modulation pattern is then uniquely identified as coming from the corresponding pixel. Thus, the present invention identifies where in the image the THz data is coming from. It is then up to the user on how to use this information.

Execution of the sequences of instructions contained in main memory 206 causes processor 202 to perform processes that will be described later. Alternatively, hardwired circuitry may be used in place of or in combination with software instructions to implement processes consistent with the present invention. Thus, the present invention is not limited to any specific combination of hardware circuitry and software.

Figure 2A:
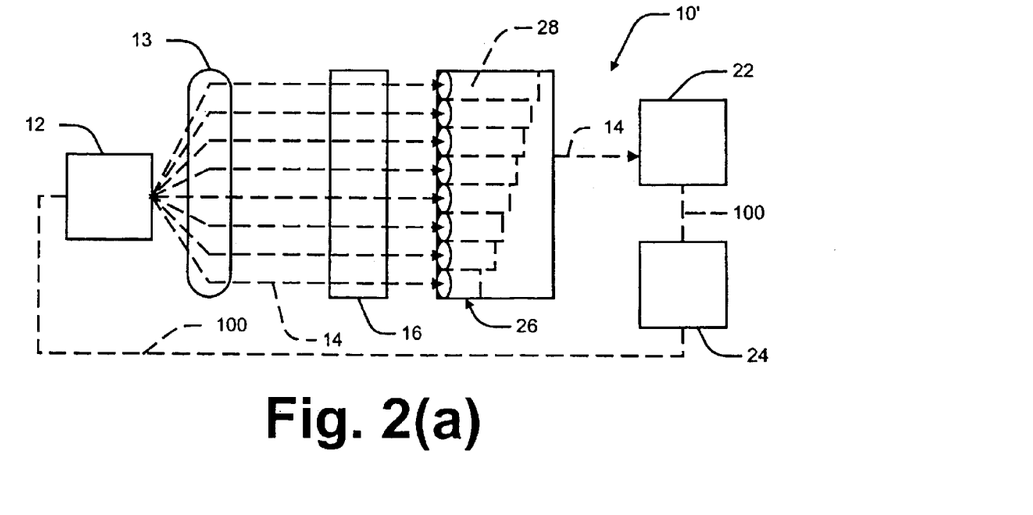
FIG. 2(a) is a schematic elevational view showing a system for THz imaging and utilizing a single THz detector and a mask having an array of pixels, wherein each pixel is a composite of two materials with different depths, in accordance with another embodiment of the present invention.
Figure 2B:
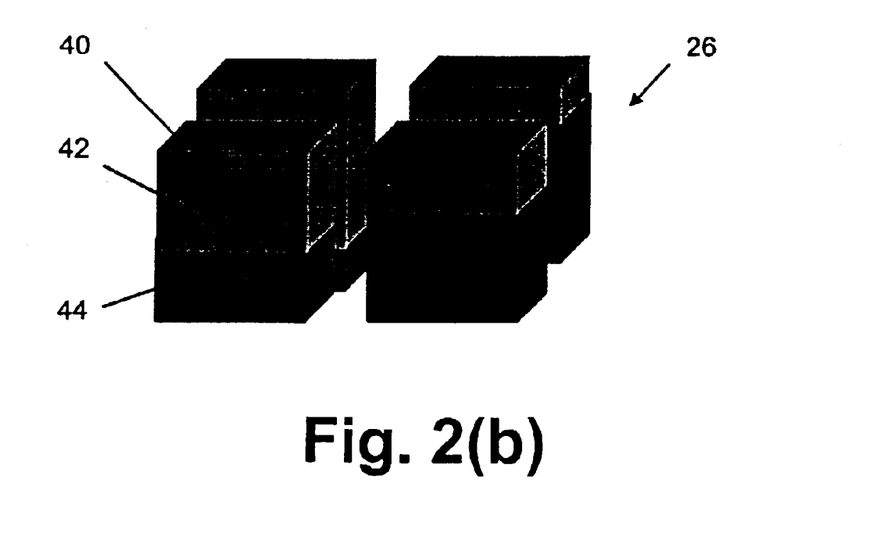
FIG. 2(b) is a schematic elevational view showing a four-pixel mask capable of use in the system shown in FIG. 2(a)
Figure 2C:
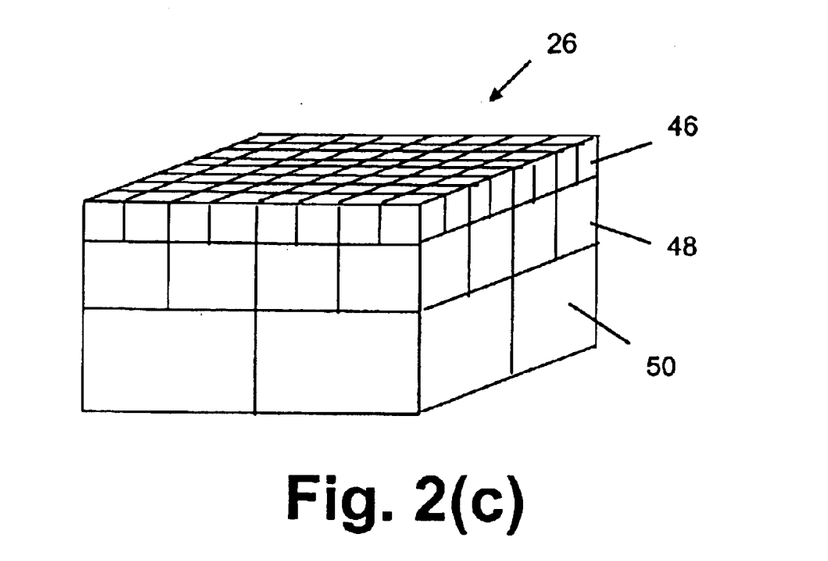
FIG. 2(c) is a schematic elevational view showing a multi-pixel, two-by-two (2×2) array, cascaded mask capable of use in the system shown in FIG. 2(a)

Referring now specifically to the drawings, a THz imaging system according to another embodiment of the present invention is illustrated in FIG. 2(a) and shown generally as reference numeral 10'. The operation and components of the THz imaging system 10' shown in FIG. 2(a) are identical to the THz imaging system 10 shown in FIG. 1, except that THz fiber bundle 20 is replaced with a mask 26 that imparts a different time delay on each pixel. Therefore, the spatial information is converted to time information in the form of time delays. Mask 26 may have a variety of configurations as shown in FIGS. 2(a)–(c). As shown in FIG. 2(a), mask 26 may have an array of holes 28 with each hole 28 having a different depth.

THz pulses 14 pass through object 16, are collected by mask holes 28, and are transmitted to THz detector 22. Each mask hole 28 imparts a different time delay on the THz pulse 14 traveling inside. The amount of time delay through each mask hole 28 may be controlled by changing the depth l of the mask hole 28.

Although only eight mask holes 28 are shown in a linear array in FIG. 2(a), any number and arrangement of mask holes 28 may be provided. The number and geometry of mask holes 28 only depend upon the size and geometry of the imaging area required. Thus, if an N×M array resolution is needed, then an N×M array of mask holes 28 should be used. Furthermore, although FIG. 2(a) shows mask 26 and THz detector 22 being arranged on the opposite side of object 16 as THz transmitter 12 (transmission mode), mask 26 and THz detector 22 may also be provided on the same side of object 16 as THz transmitter 12 to capture reflected THz beams 14 (reflective mode).

FIG. 2(b) shows another exemplary mask 26 that may be used with the present invention. In this example, a four-pixel mask in the form of a 2×2 array is used to illustrate how the time delay of each pixel may be varied. Each pixel 40 is a composite of two material layers 42, 44 with different refractive indices n. Empty space or a hole would be a material with refractive index n=1. The time t it takes for THz pulses 14 to travel through a material of thickness l and having refractive index n is t=cl/n, where c is the speed of light. The total time it takes for THz pulses 14 to travel through any pixel is $t=cl_1/n_1+cl_2/n_2$, where the subscript indicates the two materials 42 and 44, respectively. Therefore, by varying the thickness of the two materials 42, 44 in each pixel, a different time delay for each pixel may be created. This principle can be extended to a mask with more pixels. Furthermore, the configuration is not limited to two materials, but may have more than two.

FIG. 2(c) shows another exemplary mask 26 capable of use with the present invention. The mask in this example has more pixels using the 2×2 array and the concept of cascading. Cascading refers to the layering of masks with different resolution. As shown in FIG. 2(c), three material layers 46, 48, 50 are provided for mask 26, with layer 46 having sixty-four pixels, layer 48 having sixteen pixels, and layer 50 having four pixels. Thus, mask 26 may have sixty-four pixels where a THz pulse 14 may traveling through one of the sixty-four pixels in layer 46, then through one of the sixteen pixels in layer 48, and finally through one of the four pixels in layer 50. The amount of time delay changes from layer to layer depending upon the materials making up layers 46, 48, and 50. Cascading permits easier fabrication of a mask having more pixels. Cascading may also be implemented using any basic array (e.g., N×M) instead of a 2×2 array.

Figure 3:
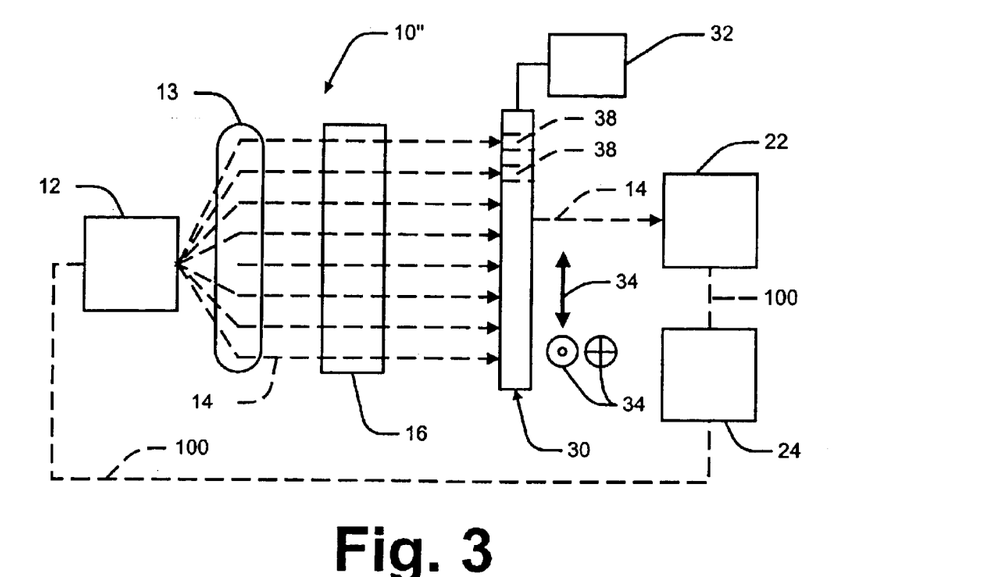
FIG. 3 is a schematic elevational view showing a system for THz imaging and utilizing a single THz detector and a plate containing a mask array in accordance with still another embodiment of the present invention.

Referring now specifically to the drawings, a THz imaging system according to still another embodiment of the present invention is illustrated in FIG. 3 and shown generally as reference numeral 10". The operation and components of the THz imaging system 10" shown in FIG. 3 are identical to the THz imaging system 10 shown in FIG. 1, except that THz fiber bundle 20 is replaced with a plate 30 having an array of masks 36 having holes 38, and movable by a motor 32 and translating stage (not shown) in directions indicated by arrows 34 (vertically or in and out of the page).

Figure 5:
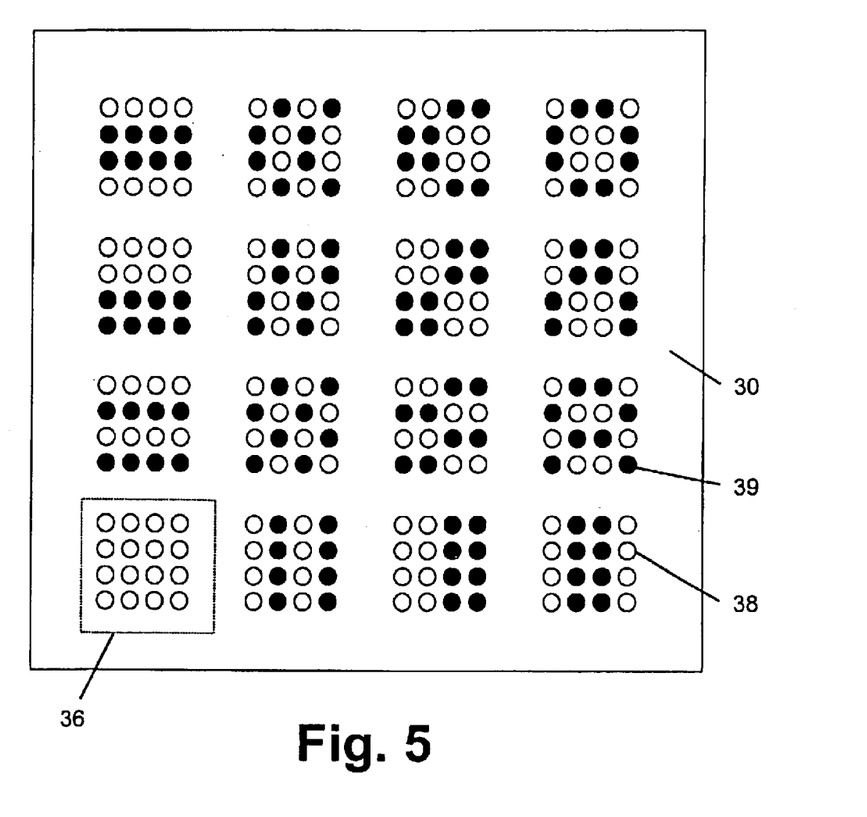
FIG. 5 is a front view of a plate containing the masks shown in FIG. 3, wherein each mask is a 4×4 array of holes (for demonstrative purposes), and the absence of a hole in the mask is shown as a filled circle.

This arrangement provides a variation of the conventional narrow beam approach. The THz energy from THz transmitter 12 is forced to pass through the holes 38 to reach the THz detector 22. Having many masks 36, with holes 38 at different spatial locations (as shown in FIG. 5), provides the spatial resolution of an array imager. There is a requirement that there can only be one hole 38 per mask 36 since there is only one THz detector 22. Conventionally, a series of masks, each mask having one hole, would be used. The hole location would be different for each mask so that measurements taken with the series of masks would provide an image of the object. If there is more than one hole 38, the THz detector 22 will not differentiate which hole 38 per mask the THz energy is coming from. However with the present invention, many holes 38 can be on the same mask if each hole 38 is turned on (i.e., presence of a hole) and off (i.e., absence of a hole) with a distinct pattern from all the other holes 38 through a series of masks. Even though there is still only one THz detector 22, which hole 38 the THz energy is coming from may be identified because the distinct on and off pattern of each hole 38 is known. This is the principle of Hadamard transform. The advantage of Hadamard transform over a single hole (or pixel) mask is the increased signal-to-noise ratio.

The Hadamard transform concept is a well-known spectral (spatial) multiplexing technique that has been widely applied in optical spectroscopy, FTIR spectroscopy, time-of-flight mass spectrometry, neutron scattering, and molecular beam-surface scattering. Hadamard transform has also been used in digital signal/image processing. The basic principle of the Hadamard transform THz imager is the unique modulation of each pixel in the image such that demodulation of the detected signal will yield the information content of each pixel. It is similar to the concept of a lock-in amplifier where the detector locks in on the modulation frequency of the transmitter to increase the signal-to-noise ratio. When the amplitude modulation is continuous, this is known as Fourier transform multiplexing. Since it is difficult to implement continuous modulation in most systems, a binary version of the Fourier transform known as the Hadamard transform is used. Below describes how the Hadamard transform may be applied to obtain an image from the THz signals measured with a single THz detector.

The Hadamard matrix has many forms, but the pseudo-random S matrix is the most widely employed. For example, the Sylvester-type Hadamard matrix $H_n$ may be used, which is a square matrix with $2^n$ rows and columns. This matrix can be generated recursively from $$H_1 = \begin{pmatrix} 1 & 1 \\ 1 & -1 \end{pmatrix}$$

and the following equation:

$$H_n = \begin{pmatrix} H_{n-1} & H_{n-1} \\ H_{n-1} & -H_{n-1} \end{pmatrix}. \tag{1}$$

The rows (columns) of the above matrix are orthogonal to each other. The matrix is also symmetric, so that:

$$H_n^{-1}H_n = \frac{1}{2^n}H_nH_n = I. \qquad (2)$$

Because of the orthogonality of the Hadamard matrix, it can be used to modulate the signals coming from the pixels of an image, and equation (2) may be used to demodulate to obtain the pixel information. If the THz signal coming from the pixels of an image is detected by a column vector $a=(a_1, a_2, \ldots, a_n)^T$, then the modulated signal b, measured by the detector, is given by:

$$b = H_n a \qquad (3)$$

The pixel information may be recovered by multiplying the measured signal with the inverse of the Hadamard matrix:

$$a = H_n^{-1}b = \frac{1}{2^n}H_n b. \qquad (4)$$

Each element of the matrix H (which is either a 1 or −1) corresponds to whether a pixel's signal adds or subtracts from the total signal at the detector. Therefore, to apply the Hadamard transform given by the matrix $H_n$ experimentally, one would need two detectors and would have to add/subtract the signal from the two detectors, depending on whether the element of the matrix is a 1 or −1. For a single detector system, a variation of the matrix H can be used where the −1 element is replaced by 0 and corresponds to a pixel having no contribution (being in the OFF state). Denoting this modified matrix as $\tilde{H}_n$, the measured signal b may be given by:

$$b = \tilde{H}_n a \qquad (5)$$

The demodulation to obtain the pixel information is a little more complex. The signal a is obtained by first noticing that $H_n\tilde{H}_n$ is diagonal except for the first row:

$$H_n\tilde{H}_n = \begin{pmatrix} 2^n & 2^{n-1} & 2^{n-1} & \cdots & 2^{n-1} \\ & 2^{n-1} & & & \\ & & 2^{n-1} & 0 & \\ & & & \ddots & \\ & 0 & & \ddots & \\ & & & & 2^{n-1} \end{pmatrix}. \qquad (6)$$

This matrix product has an upper diagonal form that can be inverted by back substitution with one extra step. Thus, the demodulation to obtain a is carried out in two steps:

$$c = \frac{1}{2^{n-1}}H_n b \qquad (7)$$

$$a_i = c_i \text{ for } i \neq 1$$

$$a_1 = \frac{1}{2}\left(c_1 - \sum_{i=2}^{2^n} c_i\right). \qquad (8)$$

To modulate a THz beam, a series of aluminum masks may be used with holes permitting or blocking the transmission of the THz beam. For exemplary purposes, a 4×4 array of holes may be used, with each hole having a diameter of 1.5 mm, and the spacing between holes being 0.5 mm. The size of the hole is chosen to coincide with the peak transmission frequency (wavelength) of the THz system (approximately 0.2 THz or 1.5 mm). Since there are sixteen pixels in the array, there will be sixteen masks corresponding to the sixteen rows of the matrix $\tilde{H}_4$. All sixteen masks may be fabricated on a single aluminum plate that is mounted on a translating stage. The THz beam from the THz transmitter may pass through a collimating lens, the sample, the mask, a focusing lens, and reach the THz detector. Sixteen measurements, each with a different mask in the beam path, may be made for each sample. The data may then be demodulated to obtain the THz signal from each pixel.

FIG. 5 shows a plate 30 containing masks 36, with each mask having a 4×4 array of holes 38 or no holes 39. For demonstrative purposes only, plate 30 is shown to hold a 4×4 array of masks 36. There may be a multitude of different masks 36 in plate 30, the number of masks 36 and the number of holes 38 being dependent upon the desired number of THz beams 14 (pixels) to be transmitted through or reflected from object 16. Each pixel (hole 38 or no hole 39) has a distinct on/off pattern as represented by the series of masks 36. Absence of a hole 38 (a no hole 39) corresponds to a pixel in the off mode. The on/off pattern for each pixel can be Hadamard (as in FIG. 5), S-matrix, or random. This principle may be generalized to an N×M array.

Although FIG. 3 shows plate 30 and THz detector 22 being arranged on the opposite side of object 16 as THz transmitter 12 (transmission mode), plate 30 and THz detector 22 may also be provided on the same side of object 16 as THz transmitter 12 (reflective mode). In the transmission mode, object 16 may be placed between THz transmitter 12 and plate 30 or between plate 30 and THz detector 22. Each mask 36 may be positioned behind or in front of object 16 by a translator stage (not shown), and data taken. The various masks 36 of plate 30 may be moved into position by a translation stage (not shown), and data may be taken by computer 24.

Each mask 36 shown in FIG. 5 may have sixteen holes or pixels. Since there is only one THz detector 22 and the THz pulses 14 from these holes arrive at THz detector 22 roughly the same time, the detector cannot determine what is coming from each hole. Therefore an image cannot be obtained. The present invention permits identification of the THz energy coming from each hole or pixel.

To see how the present invention obtains the data for each pixel, a simple example of two pixels or holes is provided. In this example, four masks are used to create two patterns (one for each hole). If, for example, the first hole has a pattern of ON/OFF/ON/OFF, and the second hole has a pattern ON/ON/OFF/OFF. If a value of "1" is assigned when the pixel is ON and a value of "−1" is assigned when the pixel is OFF, then the two patterns become 1/−1/1/−1 and 1/1/−1/−1. If the elements of each pattern are multiplied and summed, then the result is zero (i.e., 1×1+−1×1+1×−+−1×−1=0). This means that the patterns are orthogonal or distinct from each other. If each pattern is multiplied with itself and summed, then the result is four (i.e., 1×1+−1x−1+1×1+−1×−1=4 and 1×1+1×1+−1×−1+−1×−1=4), and not zero. To obtain the data for each pixel from the data obtained with all of the masks involves multiplying the mask data with the modulation pattern of that pixel. For the plate 30 shown in FIG. 5, there are sixteen data sets (one for each mask) and there are sixteen pixels corresponding to the sixteen holes or pixels/no holes in each mask. Each pixel has its own "1" and "−1" pattern, and the sixteen data sets are multiplied with this pattern and summed to get the data for that pixel. This is an over-simplified, exemplary explanation of the data analysis performed by the present invention. From the data sets for all the masks, the THz data coming from each individual pixel (hole) can be obtained by appropriate combination of the data in each set. In the example shown in FIG. 5, where the modulation pattern is a Hadamard matrix, the Hadamard transform is used to obtain pixel-level data. A rigorous mathematical description was given above in equations (1) through (8).

Figure 4:
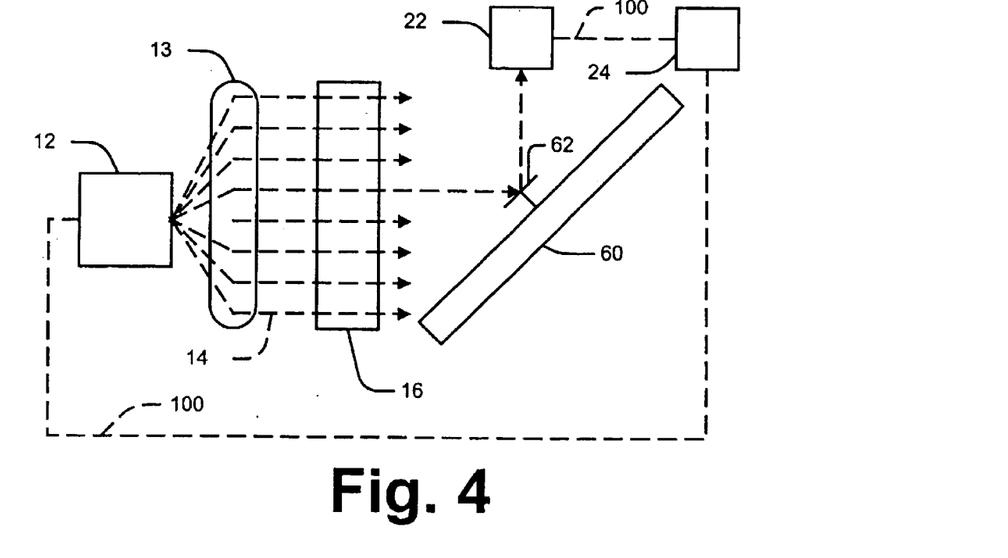
FIG. 4 is a schematic elevational view showing a system for THz imaging and utilizing a single THz detector and a micro-mirror array in accordance with still another embodiment of the present invention.

One variation of this arrangement may be to use a spatial light modulator to turn pixels 38 on and off electronically. This would eliminate the need for different masks 36 and a translating stage. Another variation would be to use a micro-mirror array 60 having an array of micro-mirrors 62 to turn pixels on and off electronically, as shown in FIG. 4. Micro-mirror array 60 would replace plate 30 and masks 36 of FIG. 3, and eliminate the need for the translating stage. This set up may operate in the reflective mode (i.e., with micro-mirror array 60 and THz detector 22 being provided on the same side of object 16 as THz transmitter 12), or in the transmission mode (i.e., with micro-mirror array 60 and THz detector being provided on the opposite side of object 16 as THz transmitter 12) that is shown in FIG. 4.

Still another embodiment of the invention is to combine the time-multiplexing technique with the pixel-modulation technique. This would involve combining the embodiments shown in FIGS. 1, 2(a), 2(c), and/or 2(c) with the embodiments shown in FIGS. 3–5. The time multiplexing maybe used for coarse resolution, while the pixel modulation may be used for fine resolution, or vice versa.

The system and method of the present invention may also be used for passive THz imaging where the THz energy emitted from an object is directly measured without the need for a THz transmitter 12 or other secondary source of THz energy. All objects emit radiation above absolute zero. The intensity and frequency of the radiation change with the temperature of the object according to Planck's law. That is why an object glows as its temperature increases. From 0° C. to 800° C. the peak emission from an object is in the THz range. Thus, the THz energy from most objects may be seen with a sensitive THz detector.

Figure 7:
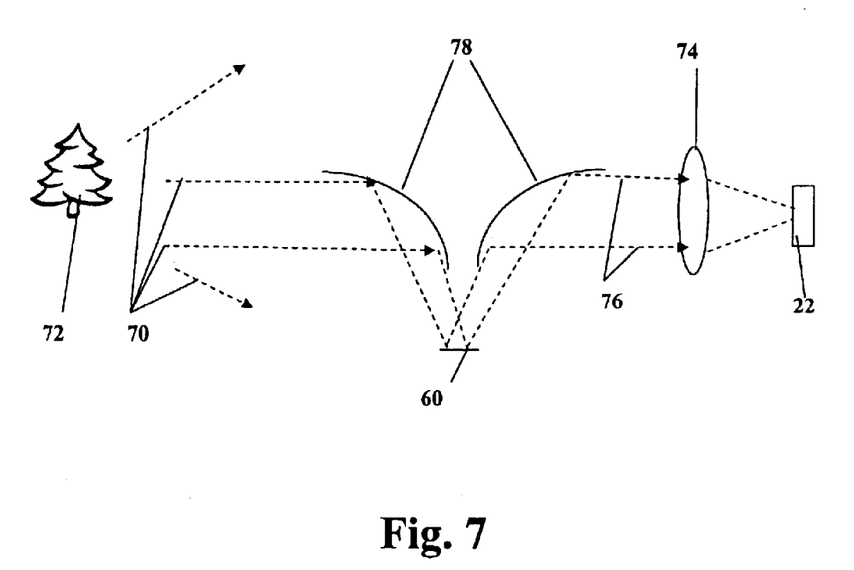
FIG. 7 is a schematic elevational view showing a system for passive THz imaging that utilizes a single THz detector and micro-mirror array in accordance with an embodiment of the present invention.

A passive THz imaging system using a single THz detector 22 in accordance with the present invention is shown in FIG. 7. THz emission 70 from an object 72 may be reflected with a parabolic mirror 78 onto a micro-mirror array 60. The micro-mirror array 60 reflects with another parabolic mirror 78 the THz energy 76 towards (an "on" state) or away from (an "off" state) a focusing lens 74 and THz detector 22. Movable individual mirrors of micro-mirror array 60 may be used to turn pixels on and off for Hadamard transform multiplexing. The passive imaging system of FIG. 7 may connect to computer 24 in the same manner discussed above for FIGS. 1–4. Micro-mirror array 60 may be replaced with the plate 30 with an array of masks 36 shown in FIGS. 3 and 5.

It will be apparent to those skilled in the art that various modifications and variations can be made in the system and method for terahertz imaging using a single terahertz detector of the present invention and in construction of the system and method without departing from the scope or spirit of the invention. Examples of such modifications have been previously provided.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A system for imaging an object emitting a plurality of terahertz pulses, the system comprising:
   means for collecting the plurality of terahertz pulses and imparting a different modulation pattern on each of the plurality of terahertz pulses;
   a single terahertz detector for receiving each of the plurality of terahertz pulses having different modulation patterns and generating electrical signals corresponding to each of the plurality of terahertz pulses having different modulation patterns;
   memory means for storing the electrical signals outputted by the terahertz detector; and
   means for processing the stored electrical signals in the memory means, wherein the processing means is electrically coupled to the memory means and calculates an image of the object.

2. A system for imaging an object emitting a plurality of terahertz pulses, as recited in claim 1, wherein the collecting means comprises a plate containing a plurality of different masks.

3. A system for imaging an object emitting a plurality of terahertz pulses, as recited in claim 2, wherein the plate is moveable in relation to the object.

4. A system for imaging an object emitting a plurality of terahertz pulses, as recited in claim 2, wherein each mask has a distinct on/off pattern which imparts a different modulation pattern on each of the plurality of the terahertz pulses.

5. A system for imaging an object emitting a plurality of terahertz pulses, as recited in claim 4, wherein the on/off pattern for each mask is one of Hadamard, S-matrix, or random.

6. A system for imaging an object emitting a plurality of terahertz pulses, as recited in claim 1, wherein the collecting means comprises a plate containing a plurality of masks having a plurality of holes which may be turned on and off.

7. A system for imaging an object emitting a plurality of terahertz pulses, as recited in claim 6, wherein each mask has a distinct on/off pattern of holes which imparts a different modulation pattern on each of the plurality of the terahertz pulses.

8. A system for imaging an object emitting a plurality of terahertz pulses, as recited in claim 1, wherein the system images a large area of the object.

9. A system for imaging an object emitting a plurality of terahertz pulses, as recited in claim 1, wherein the collecting means comprises a micro-mirror array containing a plurality of micro-mirrors.

10. A method for imaging an object emitting a plurality of terahertz pulses, the method comprising:
   collecting the plurality of terahertz pulses and imparting a different modulation pattern on each of the plurality of terahertz pulses;
   receiving each of the plurality of terahertz pulses having different modulation patterns with a single terahertz detector;
   generating electrical signals corresponding to each of the plurality of terahertz pulses having different modulation patterns;
   storing the electrical signals; and
   processing the stored electrical signals and calculating an image of the object.

11. A system for obtaining imaging data of an object emitting a plurality of terahertz pulses, the system comprising:
   means for collecting the plurality of terahertz pulses and imparting a different modulation pattern on each of the plurality of terahertz pulses; and
   a single terahertz detector for receiving each of the plurality of terahertz pulses having different modulation patterns and generating electrical signals corresponding to each of the plurality of terahertz pulses having different modulation patterns.

12. A method for obtaining imaging data of an object emitting a plurality of terahertz pulses, the method comprising:
   collecting the plurality of terahertz pulses and imparting a different modulation pattern on each of the plurality of terahertz pulses;

receiving each of the plurality of terahertz pulses having different modulation patterns and generating electrical signals corresponding to each of the plurality of terahertz pulses having different modulation patterns.

13. A system for imaging an object emitting a plurality of terahertz pulses, the system comprising:
- a plate containing a plurality of different masks for collecting the plurality of terahertz pulses and imparting a different modulation pattern on each of the plurality of terahertz pulses;
- a single terahertz detector for receiving each of the plurality of terahertz pulses having different modulation patterns and generating electrical signals corresponding to each of the plurality of terahertz pulses having different modulation patterns;
- a computer memory for storing the electrical signals outputted by the terahertz detector; and
- a computer processor for processing the stored electrical signals in the computer memory, wherein the computer processor is electrically coupled to the computer memory and calculates an image of the object.

14. A system for imaging an object emitting a plurality of terahertz pulses, the system comprising:
- a plate containing a plurality of masks having a plurality of holes for collecting the plurality of terahertz pulses and imparting a different modulation pattern on each of the plurality of terahertz pulses;
- a single terahertz detector for receiving each of the plurality of terahertz pulses having different modulation patterns and generating electrical signals corresponding to each of the plurality of terahertz pulses having different modulation patterns;
- a computer memory for storing the electrical signals outputted by the terahertz detector; and
- a computer processor for processing the stored electrical signals in the computer memory, wherein the computer processor is electrically coupled to the computer memory and calculates an image of the object.

15. A system for imaging an object emitting a plurality of terahertz pulses, the system comprising:
- a micro-mirror array containing a plurality of micro-mirrors for collecting the plurality of terahertz pulses and imparting a different modulation pattern on each of the plurality of terahertz pulses;
- a single terahertz detector for receiving each of the plurality of terahertz pulses having different modulation patterns and generating electrical signals corresponding to each of the plurality of terahertz pulses having different modulation patterns;
- a computer memory for storing the electrical signals outputted by the terahertz detector; and
- a computer processor for processing the stored electrical signals in the computer memory, wherein the computer processor is electrically coupled to the computer memory and calculates an image of the object.

* * * * *

UNITED STATES PATENT AND TRADEMARK OFFICE
CERTIFICATE OF CORRECTION

PATENT NO. : 6,909,095 B2 Page 1 of 1
APPLICATION NO. : 10/454152
DATED : June 21, 2005
INVENTOR(S) : Phuc G. Tran et al.

It is certified that error appears in the above-identified patent and that said Letters Patent is hereby corrected as shown below:

Title page,
Item [*] Notice, insert:
-- This patent issued on a continued prosecution application filed under 37 CFR 1.53(d), and is subject to the twenty year patent term provisions of 35 U.S.C. 154(a)(2).

This patent is subject to a terminal disclaimer. --.

Signed and Sealed this

Fourth Day of July, 2006

JON W. DUDAS
*Director of the United States Patent and Trademark Office*